United States Patent

Frei et al.

Patent Number: 4,696,945
Date of Patent: Sep. 29, 1987

[54] 13β-MILBEMYCIN DERIVATIVES FOR CONTROLLING ECTO- AND ENDOPARASITES OF PLANTS AND ANIMALS

[75] Inventors: Bruno Frei, Liestal; Anthony C. O'Sullivan, Basel, both of Switzerland

[73] Assignee: Ciba-Geigy Corporation, Ardsley, N.Y.

[21] Appl. No.: 885,066

[22] Filed: Jul. 14, 1986

Related U.S. Application Data

[63] Continuation of Ser. No. 803,354, Dec. 2, 1985, abandoned.

[30] Foreign Application Priority Data

Dec. 4, 1984 [CH] Switzerland ............. 05750/84

[51] Int. Cl.⁴ .................. C07D 315/00; C07D 311/96; A61K 31/365
[52] U.S. Cl. .................... 514/450; 549/264; 549/265; 549/268
[58] Field of Search .............. 514/450; 549/264, 265

[56] References Cited

U.S. PATENT DOCUMENTS 4,200,581  4/1980  Fisher et al. .............. 549/264
4,587,247  5/1986  Linn ...................... 514/222

FOREIGN PATENT DOCUMENTS 0001689  5/1979  European Pat. Off. ......... 549/264
0074758  3/1983  European Pat. Off. ......... 549/264

OTHER PUBLICATIONS

J. Am. Chem. Soc. 103: pp. 4221-4224, (1981).
Science, 221: pp. 823-828, (Aug. 26, 1983).
J. Org. Chem. 47: pp. 489-492, (1982).
The Avermectin Family of Macrolide-Like Antibiotics in Macrolide Antibiotics, Academic Press pp. 553-606, (1984).

Primary Examiner—Glennon H. Hollrah
Assistant Examiner—D. Dinner
Attorney, Agent, or Firm—Meredith C. Findlay; Edward McC. Roberts

[57] ABSTRACT

The invention relates to parasiticidally and insecticidally highly active compounds of formula I

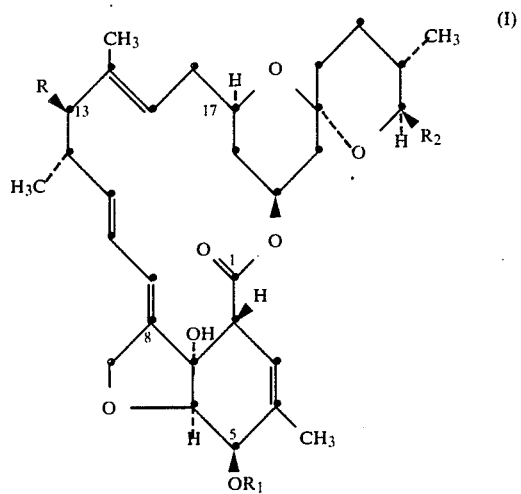

wherein
$R_1$ is hydrogen or a protecting group;
$R_2$ is methyl, ethyl, isopropyl or sec-butyl; and
R is a radical $R_3$ which is bound through oxygen or sulfur and is selected from the group consisting of $C_1-C_{10}$alkyl, $C_1-C_{10}$haloalkyl, $C_1-C_{10}$hydroxyalkyl, $C_1-C_{10}$mercaptoalkyl, $C_2-C_{10}$alkoxyalkyl, $C_3-C_{10}$alkoxyalkoxyalkyl, hydroxy- or mercapto-substituted $C_3-C_{10}$alkoxyalkyl, $C_4-C_{15}$alkoxyalkoxyalky, hdroxy- or mercapto-substituted $C_4-C_{15}$alkoxyalkoxyalkyl, $C_2-C_{10}$-alkenyl, $C_2-C_{10}$haloalkenyl, $C_2-C_{10}$alkynyl, $C_2-C_{10}$haloalkynyl, phenyl which is unsubstituted or substituted by halogen, $C_1-C_3$-alkyl, $C_1-C_3$haloalkyl, $C_1-C_3$alkoxy, $C_1-C_3$haloalkoxy, cyano and/or nitro, and benzyl which is unsubstituted or substituted by halogen, $C_1-C_3$alkyl, $C_1-C_3$haloalkyl, $C_1-C_3$alkoxy, $C_1-C_3$haloalkoxy, cyano and/or nitro, or R is one of the groups —SH or —S—C(O)OR$_4$, wherein $R_4$ is $C_1-C_{10}$haloalkyl, or a phenyl or benzyl group which is unsubstituted or substituted by halogen, $C_1-C_3$alkyl, $C_1-C_3$haloalkyl, $C_1-C_3$alkoxy, $C_1-C_3$haloalkoxy, cyano and/or nitro, and to the preparation thereof starting from suitably substituted 15-hydroxy- or 13β-hydroxymilbemycins of formula II.

15 Claims, No Drawings

13β-MILBEMYCIN DERIVATIVES FOR CONTROLLING ECTO- AND ENDOPARASITES OF PLANTS AND ANIMALS

This is a continuation of application Ser. No. 803,354 filed on Dec. 2, 1985, now abandoned.

The present invention relates to novel 13β-milbemycin derivatives of formula I below, to the preparation thereof and to the use thereof for controlling pests such as ecto- and endoparasites. The compounds of the invention are 13β-milbemycins of the general formula I

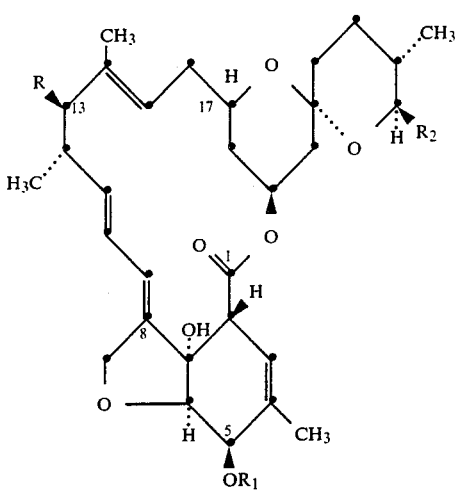

wherein
$R_1$ is hydrogen or a protecting group;
$R_2$ is methyl, ethyl, isopropyl or sec-butyl; and
R is a radical $R_3$ which is bound through oxygen or sulfur and is selected from the group consisting of $C_1$–$C_{10}$alkyl, $C_1$–$C_{10}$haloalkyl, $C_1$–$C_{10}$hydroxyalkyl, $C_1$–$C_{10}$mercaptoalkyl, $C_2$–$C_{10}$alkoxyalkyl, $C_3$–$C_{10}$ alkoxyalkoxyalkyl, hydroxy- or mercapto-substituted $C_3$–$C_{10}$alkoxyalkoxyalkyl, $C_4$–$C_{15}$alkoxyalkoxyalkoxyalkyl, hydroxy- or mercapto-substituted $C_4$–$C_{15}$alkoxyalkoxyalkoxyalkyl, $C_2$–$C_{10}$alkenyl, $C_2$–$C_{10}$haloalkenyl, $C_2$–$C_{10}$alkynyl, $C_2$–$C_{10}$haloalkynyl, phenyl which is unsubstituted or substituted by halogen, $C_1$–$C_3$-alkyl, $C_1$–$C_3$-haloalkyl, $C_1$–$C_3$alkoxy, $C_1$–$C_3$haloalkoxy, cyano and/or nitro, and benzyl which is unsubstituted or substituted by halogen, $C_1$–$C_3$alkyl, $C_1$–$C_3$haloalkyl, $C_1$–$C_3$alkoxy, $C_1$–$C_3$haloalkoxy, cyano and/or nitro, or R is one of the groups —SH or —S—C(O)$R_4$, wherein $R_4$ is $C_1$–$C_{10}$alkyl, $C_1$–$C_{10}$haloalkyl, or a phenyl or benzyl group which is unsubstituted or substituted by halogen, $C_1$–$C_3$alkyl, $C_1$–$C_3$haloalkyl, $C_1$–$C_3$alkoxy, $C_1$–$C_3$haloalkoxy, cyano and/or nitro.

Depending on the number of carbon atoms indicated, alkyl by itself or as moiety of another substituent will be understood as meaning for example the following groups: methyl, ethyl, propyl, butyl, pentyl, hexyl, heptyl, octyl, nonyl, decyl etc. and the isomers thereof, e.g. isopropyl, sec-butyl, isobutyl, tert-butyl, isopentyl etc. Haloalkyl is a mono- to perhalogenated alkyl substituent, e.g. $CHCl_2$, $CHF_2$, $CH_2Cl$, $CCl_3$, $CH_2F$, $CH_2CH_2Cl$, $CHBr_2$ etc., preferably $CF_3$. Throughout this specification, halogen will be understood as meaning fluorine, chlorine, bromine or iodine, preferably fluorine, chlorine or bromine. Haloalkoxy is a haloalkyl radical which is bound through oxygen and, as stated above, may be halogenated. Alkenyl is an aliphatic hydrocarbon radical which is characterised by at least one C=C double bond, e.g. vinyl, propen-1-yl, allyl, buten-1-yl, buten-2-yl, buten-3-yl etc. Haloalkenyl is therefore such an alkenyl radical which is substituted by one or more halogen atoms. Alkynyl is a straight or branched carbon chain which is characterised by at least one C≡C triple bond. Typical representatives are: ethynyl, propion-1-yl, propargyl, butyn-1-yl etc. $C_2$–$C_{10}$alkoxyalkyl is an unbranched or branched $C_2$–$C_{10}$alkyl group which is interrupted by an oxygen atom, e.g. $CH_2OCH_3$, $CH_2CH_2OCH_3$, $CH_2CH(CH_3)OCH_3$, $CH_2OC_2H_5$, $CH_2OC_3H_7$—i, $CH_2CH_2CH_2OCH_3$ etc. $C_3$–$C_{10}$alkoxyalkoxyalkyl is an unbranched or branched $C_3$–$C_{10}$alkyl group which is interrupted at each of two positions by an oxygen atom. Typical examples are: $CH_2OCH_2OCH_3$, $CH_2CH_2OCH_2OCH_3$, $CH_2OCH_2CH_2OCH_3$, $CH_2OCH_2OC_2H_5$, $CH(CH_3)OCH_2OC_3H_7$—i etc. $C_4$–$C_{15}$alkoxyalkoxyalkoxyalkyl is an unbranched or branched $C_4$–$C_{15}$alkyl group which is interrupted at each of 3 positions by an oxygen atom, e.g. $CH_3OCH_2OCH_2OCH_2$, $CH_3OCH_2CH_2OCH_2OCH_2$, $CH_3OCH_2CH_2OCH_2CH_2OCH_2CH_2$etc. Throughout this specification, OH protecting groups $R_1$ will be understood as meaning the customary protective functions in organic chemistry. Such protecting groups are in particular acyl and silyl groups. Examples of suitable acyl groups are the radicals $R_4'$—C(O)—, wherein $R_4'$ has the meanings given for $R_4$ under formula I and is preferably $C_1$–$C_6$alkyl, $C_1$–$C_6$haloalkyl, or phenyl which is unsubstituted or substituted by halogen, $C_1$–$C_3$alkyl, $CF_3$ or nitro. Suitable silyl groups $R_1$ are the radicals —Si($R_5$)($R_6$)($R_7$), wherein $R_5$, $R_6$ and $R_7$, preferably independently, are each $C_1$–$C_4$alkyl, benzyl or phenyl and form for example one of the groups trimethylsilyl, tris(tert-butyl)silyl, diphenyl-tert-butylsilyl, bis-(isopropyl)methylsilyl, triphenylsilyl etc. and, in particular, tert-butyldimethylsilyl. The 5—OH group may also occur as benzyl ether or methoxyethoxymethyl ether.

Throughout this specification, compounds wherein $R_2$ is sec-butyl will also be considered as belonging to the class of milbemycin derivatives although according to conventional classification they do not belong to this class but, in accordance with U.S. Pat. No. 4,173,571, are derived from avermectin derivatives.

Compounds of formula I wherein $R_1$ is a protecting group can be converted by simple, e.g. hydrolytic, removal of the protective function into the highly active 5-hydroxy derivative ($R_1$=H) and act therefore as intermediates. However, the biological value of these compounds is intrinsically not diminished by the protecting group.

In naturally occurring milbemycins ($R_1$=H; $R_2$=$CH_3$, $C_2H_5$ or iso$C_3H_7$) the substituent R in the 13-position is always hydrogen. However, in avermectins an α-L-oleandrosyl-α-L-oleandrose radical which is bound through oxygen in the α-configuration to the macrolide molecule is in the 13-position. Moreover, avermectins differ structurally from milbemycins by the presence of a 23-OH group or $\Delta^{22,23}$ double bond and, usually, by the presence of a substituent $R_2$=sec—$C_4H_9$. By hydrolysing the sugar residue of avermectins, the corresponding avermectinaglycons containing an allylic 13α-hydroxyl group are readily obtained. In the avermectin derivatives of the present invention the $\Delta^{22,23}$ double bond always occurs in hydrogenated form.

On account of their pronounced parasiticidal and insecticidal activity, the following subgroups of compounds of formula I are particularly preferred:

An interesting group within the scope of formula I comprises those compounds wherein $R_1$ is hydrogen or a protecting group; $R_2$ is methyl, ethyl, isopropyl or sec-butyl; and R is a radical $R_3$ which is bound through oxygen or sulfur and is selected from the group consisting of $C_1$–$C_{10}$alkyl, $C_1$–$C_{10}$haloalkyl, $C_2$–$C_{10}$alkoxyalkyl, $C_3$–$C_{10}$alkoxyalkoxyalkyl, $C_2$–$C_{10}$alkenyl, $C_2$–$C_{10}$haloalkenyl, $C_2$–$C_{10}$alkynyl, $C_2$–$C_{10}$haloalkynyl, phenyl which is unsubstituted or substituted by halogen, $C_1$–$C_3$alkyl, $C_1$–$C_3$haloalkyl, $C_1$–$C_3$alkoxy, $C_1$–$C_3$haloalkoxy, cyano and/or nitro, and benzyl which is unsubstituted or substituted by halogen, $C_1$–$C_3$alkyl, $C_1$–$C_3$haloalkyl, $C_1$–$C_3$alkoxy, $C_1$–$C_3$haloalkoxy, cyano and/or nitro, or R is one of the groups —SH or —S—C(O)OR$_4$, wherein $R_4$ is $C_1$–$C_{10}$alkyl, $C_1$–$C_{10}$haloalkyl, or a phenyl or benzyl group which is unsubstituted or substituted by halogen, $C_1$–$C_3$alkyl, $C_1$–$C_3$haloalkyl, $C_1$–$C_3$alkoxy, $C_1$–$C_3$haloalkoxy, cyano and/or nitro.

Group Ia:

Compounds of formula I, wherein $R_1$ is hydrogen; $R_2$ is methyl, ethyl, isopropyl or sec-butyl; and R is a radical $R_3$ which is bound through oxygen or sulfur and is selected from the group consisting of $C_1$–$C_4$alkyl, $C_2$–$C_4$alkenyl, phenyl which is unsubstituted or substituted by fluorine, chlorine, bromine, methyl, $CF_3$, methoxy, cyano and/or nitro, and benzyl which is unsubstituted or substituted by fluorine, chlorine, bromine, methyl, $CF_3$, methoxy, cyano and/or nitro, or R is one of the groups —SH or —S—C(O)OR$_4$, wherein $R_4$ is $C_1$–$C_4$alkyl, $C_1$–$C_4$haloalkyl, or a phenyl or benzyl group each of which is unsubstituted or substituted by fluorine, chlorine, bromine, methyl, $CF_3$, methoxy, cyano and/or nitro.

Group Ib:

Compounds of formula I, wherein $R_1$ is hydrogen; $R_2$ is methyl, ethyl, isopropyl or sec-butyl; and R is a radical $R_3$ which is bound through oxygen or sulfur and is selected from the group consisting of $C_1$–$C_4$alkyl and $C_2$–$C_4$alkenyl, or R is one of the groups —SH or —S—C(O)OR$_4$, wherein $R_4$ is $C_1$–$C_4$alkyl, $C_1$–$C_4$ haloalkyl, or phenyl which is unsubstituted or substituted by fluorine, chlorine, bromine, methyl, $CF_3$, methoxy, cyano and/or nitro.

Group Ic:

Compounds of formula I, wherein $R_1$ is hydrogen; $R_2$ is methyl, ethyl, isopropyl or sec-butyl; and R is a radical $R_3$ which is bound through oxygen or sulfur and is selected from the group consisting of $C_1$–$C_4$alkyl and $C_2$–$C_4$alkenyl, or R is one of the groups —SH or —S—C(O)OR$_4$, wherein $R_4$ is $C_1$–$C_4$alkyl or $C_1$–$C_4$haloalkyl.

Group Id:

Compounds of formula I, wherein $R_1$ is hydrogen; $R_2$ is ethyl or isopropyl; and R is a radical $R_3$ which is bound through oxygen or sulfur and is $C_1$–$C_2$alkyl, or R is one of the groups —SH or —S—C(O)OR$_4$, wherein $R_4$ is $C_1$–$C_2$alkyl or $C_1$–$C_2$haloalkyl.

Group Ie:

Compounds of formula I, wherein $R_1$ is hydrogen; $R_2$ is ethyl or isopropyl; and R is a radical $R_3$ which is bound through oxygen or sulfur and is methyl, or R is one of the groups —SH or —S—C(O)OR$_4$, wherein $R_4$ is methyl.

Group If:

Compounds of formula I, wherein $R_1$ is hydrogen; $R_2$ is ethyl or isopropyl; and R is a radical $R_3$ which is bound through oxygen or sulfur and is straight chain or branched $C_1$–$C_4$ alkyl, in particular methyl or ethyl.

Examples of particularly preferred 5-hydroxy derivatives of formula I are:

13β-methoxymilbemycin D,

13β-ethoxymilbemycin D,

13β-phenylthiomilbemycin D,

13β-p-Chlorophenoxycarbonylthiomilbemycin D,

13β-mercaptomilbemycin D,

13β-methylthiomilbemycin D,

13β-tert-butylthiomilbemycin D,

13β-methylthiomilbemycin $A_4$,

13β-tert-butylthiomilbemycin $A_4$,

13β-methoxymilbemycin $A_4$,

13β-methoxymethoxymilbemycin $A_4$,

13β-Ethylthiomilbemycin $A_4$,

13β-Ethoxymilbemycin $A_4$.

Examples of preferred compounds of formula I carrying a protective function at the 5-hydroxy group are:

5-O-tert-butyldimethylsilyl-13β-methoxymilbemycin D,

5-O-tert-butyldimethylsilyl-13β-ethoxymilbemycin D,

5-O-tert-butyldimethylsilyl-13β-mercaptomilbemycin D,

5-O-tert-butyldimethylsilyl-13β-methylthiomilbemycin D.

The present invention relates not only to the compounds of formula I but also to the novel process for the preparation thereof. Surprisingly, it has been found that the allyl alcohols of formula II defined below, wherein the allylic OH group is in the 15-position of the molecule, can be etherified or thioetherified with suitable etherifying or thioetherifying agents such that the substituent R to be introduced occupies the 13β-position of the molecule stereospecifically and affords only small amounts of by-products, which are substituted in the 15-position. It has also been found that compounds of formula II containing a 13β-hydroxy group can, while retaining the 13β-orientation, be converted into 13β-ethers. The process of the present invention therefore also makes it possible to introduce selectively the substituent R defined under formula I into the 13β-position of milbemycin derivatives or 13-deoxy-22,23-dihydroavermectin derivatives and so to obtain highly effective parasiticides and insecticides which may also be used for the formation of further derivatives.

Accordingly, the present invention also relates to a process for the preparation of compounds of formula I, which process comprises treating an allyl alcohol of formula II

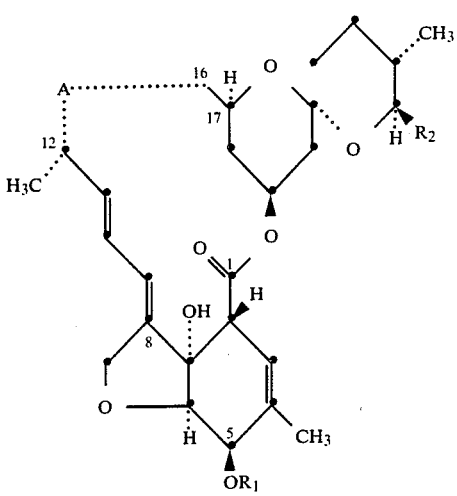

(II)

wherein A is one of the groups a or b

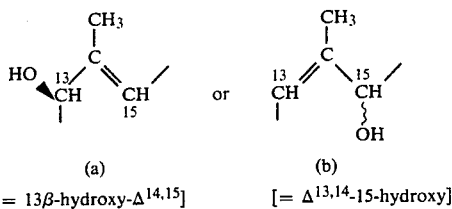

(a) [= 13β-hydroxy-Δ$^{14,15}$]

(b) [= Δ$^{13,14}$-15-hydroxy]

$R_1$ is a protecting group and $R_2$ is as defined for formula I, with a reagent suitable for the introduction of a 13β-ether or 13β-thioether group or, to introduce a 13β-mercapto group, with a halothionoformiate and then reducing the resultant product and, if free hydroxy compounds are desired, subsequently removing the protecting group $R_1$ by hydrolysis.

Throughout this specification, allyl alcohols of formula II wherein A is the group a shall be referred to as compounds of formula IIa and, accordingly, those allyl alcohols of formula II wherein A is the group b shall be referred to as compounds of formula IIb.

Examples of reagents suitable for the introduction of the 13β-ether or 13β-thioether group into compounds of formula IIb are:

(a) alcohols and thiols of formula III $$R_3\text{—XH} \qquad \text{(III)}$$

wherein $R_3$ is as defined for formula I and X is oxygen or sulfur;

(b) halothionoformiates of formula IV

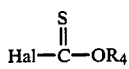

(IV)

wherein $R_4$ is as defined for formula I and Hal is halogen such as fluorine, chlorine, bromine or iodine, preferably chlorine or bromine; and (c) disulfides of formula V $$R_3\text{—SS—}R_3 \qquad \text{(V)}$$

wherein $R_3$ is as defined for formula I.

The 13β-alcohols of formula IIa can also be converted into the 13β-ethers by conventional methods, e.g. by reaction with the alcohols of formula III or with a halide $R_3$-Hal, wherein $R_3$ is as defined for formula I and Hal is a halogen atom, preferably chlorine or bromine. By an entirely analogous procedure, a thiol analogous to alcohols of formula IIa can be converted into a 13β-thioether by reaction with the halide $R_3$-Hal. Compounds of formula I, wherein R is a 13β-mercapto group can also be converted into the 13β-thioethers in conventional manner, e.g. by reaction with alkylating agents of formula III. Such reactions are etherification reactions which are known to the skilled person and represent a derivativisation of a 13β-hydroxy or 13β-mercapto group without affecting the spatial 13β-orientation of these groups.

The process is generally carried out in an inert solvent or in one of the reactants provided these are liquid. Suitable solvents are e.g.: ethers and ethereal compounds such as dialkyl ethers (diethyl ether, diisopropyl ether, tert-butylmethyl ether, dimethoxyethane, dioxane, tetrahydrofuran, anisole etc.); halogenated hydrocarbons such as chlorobenzene, methylene chloride, ethylene chloride, chloroform, carbon tetrachloride, tetrachloroethylene etc.; or sulfoxides such as dimethyl sulfoxide. Aromatic or aliphatic hydrocarbons such as benzene, toluene, xylenes, petroleum ether, ligroin, cyclohexane etc. may also be present. In some cases it may be advantageous to carry out the reaction or partial steps thereof in an inert gas atmosphere (e.g. argon, helium, nitrogen etc.) and/or in absolute solvents. If desired, intermediates may be isolated from the reaction medium and, if desired, be purified in conventional manner before further reaction, e.g. by washing, digesting, extraction, recrystallisation, chromatography etc. However, such reaction steps may be dispensed with and only carried out with the corresponding final products.

The reaction of compounds of formula II with alcohols of formula III or of compounds of formula IIb with alcohols or thiols of formula III is carried out in the presence of catalytic amounts of an acid. Protonic acids or Lewis acids may be used for the catalysis of the reaction. Examples of suitable acids are inorganic acids such as hydrohalic acid, e.g. hydrochloric acid, hydrobromic acid or hydriodic acid, chloric acid, perchloric acid, as well as sulfuric acid, phosphoric acid and phosphorous acid; and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid etc.; as well as Lewis acids such as $BF_3$, $AlCl_3$, $ZnCl_2$ etc., preferably $BF_3$ in the form of the etherate. Benzenesulfonic acid, p-toluenesulfonic acid, sulfuric acid and boron trifluoride etherate are particularly preferred. It may be advantageous to carry out this reaction additionally in the presence of an orthoester of formula VI $$R_{10}C(OR_3)_3 \qquad \text{(VI)}$$

wherein $R_3$ is as defined for formula I and $R_{10}$ is hydrogen or $C_1$-$C_6$alkyl, preferably methyl. The reaction temperatures are generally in the range from −50° to +150° C., preferably from −20° to +100° C. or at the boiling point of the solvent or of the mixture of solvents.

The reaction of compounds of formula IIb with halothionoformiates of formula IV is usually carried out in the above inert solvents or in the halothionoformiate of formula IV itself. It is convenient to carry out the reaction in the presence of a condensing agent. Suitable condensing agents are both organic and inorganic acids, e.g. tertiary amines such as trialkyl amines (trimethylamine, triethylamine, tripropylamine etc.), pyridines and pyridine bases (4-dimethylaminopyridine, 4-pyrrolidylaminopyridine etc.), with pyridine being preferred. The condensing agent is usually employed in at least equimolar amount, based on the starting materials. The reaction temperatures are generally in the range from −50° to +150° C., preferably from −20° to +100° C. The thiol carbonates of formula I (R=—S—C(O)R₄) forming during this reaction can be converted into the 13β-mercapto compounds of formula I (R=SH) by simple reduction, e.g. with zinc in glacial acetic acid. This reduction is conveniently carried out in a customary, inert, organic solvent in the temperature range from 0° to 50° C., preferably from 20° to 50° C.

The reaction of compounds of formula IIb with disulfides of formula V is carried out in the presence of an at least equimolar amount of a trivalent phosphine, e.g. triphenylphosphine, tri-n-butylphosphine, n-butyldiphenylphosphine, and in the presence of a 1/10 to 3 molar amount of an N-[SR₃]-sulfenimide, wherein R₃ is as defined for formula I. Particularly suitable sulfenimides are N-[SR₃]-succinimide and N-[SR₃]-benzosuccinimide. The reaction is conveniently carried out in an inert solvent or mixture of solvents. Suitable solvents are those mentioned above. Ths reaction is carried out in the temperature range from 0° to +50° C., preferably from +20° to +30° C.

Unless specifically stated, all starting materials employed are known compounds or compounds which can be prepared in a manner known per se, e.g. by methods analogous to those for the preparation of known representatives.

The compounds of formula IIb [=Δ$^{13,14}$-15-hydroxy] can be obtained by reacting 14,15-epoxymilbemycins of formula VII

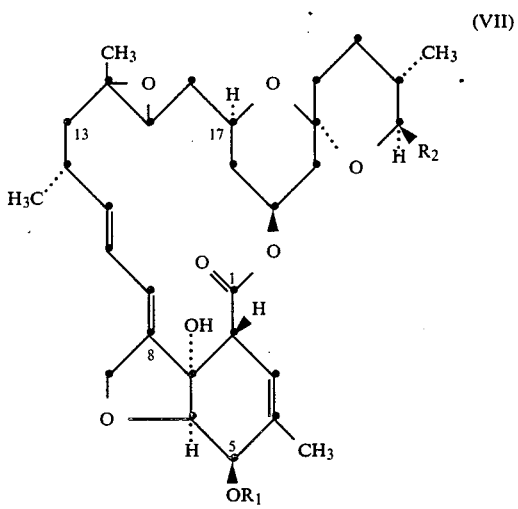

(VII)

wherein R₁ and R₂ are as defined for formula I, with the complex reagent [HN₃]$_m$/Al(ethyl)₃]$_n$, wherein m and n are each independently 1 or 2 or a value between 1 and 2, in an inert dry solvent and in the temperature range from −30° to +10° C., preferably from −20° to −5° C.

Preferred inert solvents are aliphatic and aromatic hydrocarbons such as benzene, toluene, xylene, and petroleum ether; ethers such as diethyl ether, tert-butyl methyl ether, tetrahydrofuran, dioxane, and anisole.

The reaction is conveniently carried out in an inert gas such as nitrogen or argon.

Hydrazoic acid (HN₃) can also be converted, in the nascent state, into the [NH₃]$_m$/[Al(Et)₃]$_n$ complex by suspending sodium azide in the stipulated dry solvent or mixture of solvents and generating HN₃ in the solution with a stronger acid, e.g. H₂SO₄ (preferably oleum in order to ensure absolutely dry reaction conditions). Al(Et)₃ should already be present in the solution or added thereto shortly afterwards. The epoxy compound to be reacted can also already be present in the solution or added thereto at a suitable time.

The starting compounds of formula VII, which are employed for the preparation of compounds of formula IIb, can be easily prepared by epoxidation of the compounds known from U.S. Pat. No. 3,950,360 and originally designated as "Antibiotics B-41-A", later called "milbemycin A" compounds, and of the compounds known from U.S. Pat. No. 4,346,171 and designated as "B-41-D" or "milbemycin D"; as well as of the 13-deoxy-22,23-dihydroavermectins (R₂=sec-butyl) of the formula VIII

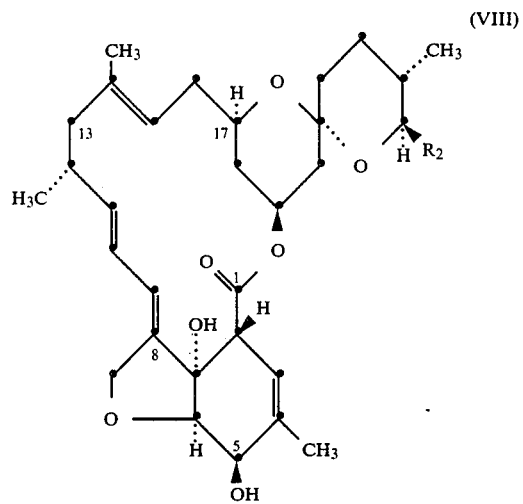

(VIII)

R₂=CH₃ milbemycin A₃
R₂=C₂H₅ milbemycin A₄
R₂=isoC₃H₇ milbemycin D
R₂=sec-C₄H₉ 13-deoxy-22,23-dihydro-C-076-B1a-aglycon, known from U.S. Pat. No. 4,173,571.

The epoxidation is carried out in a solvent phase in the temperature range from −10° to +20° C., preferably from −5° to +5° C.

Peracids such as peracetic acid, trifluoroperacetic acid, perbenzoic acid and chloroperbenzoic acid are suitable for the epoxidation.

The 13β-hydroxy-Δ$^{14,15}$ compounds of formula IIa can be prepared by reacting compounds of formula IIb, wherein R₁ is a protecting group, with pyridinium dichromate [=(Pyr)₂+Cr₂O₇]. This reaction is carried out in dimethylformamide and in the temperature range from −10° to +60° C. If desired, the protecting group $R_1$ is subsequently removed by hydrolysis.

By acylating or silylating the 5-OH group, all those derivatives of formulae I, IIa, IIb and VII are prepared wherein $R_1$ has a meaning other than hydrogen ($R_1$ = OH protecting group). The introduction of the acyl group is usually effected with the corresponding acyl halides or acyl anhydrides and is preferably employed to introduce the $R_4C(O)$-group mentioned above. For the silylation it is convenient to use a silane of the formula $Y-Si(R_5)(R_6)(R_7)$, wherein each of $R_5$, $R_6$ and $R_7$ is one of the radicals indicated above. The term acyl halide denotes acyl chloride or acyl bromide and Y is a silyl leaving group. Examples of silyl leaving groups Y are bromide, chloride, cyanide, azide, acetamide, trifluoroacetate or trifluoromethanesulfonate. This recitation constitutes no limitation; further typical silyl leaving groups are known to the skilled person.

5-O-Acylations and 5-O-silylations are carried out in anhydrous medium, preferably in inert solvents and, most preferably, in aprotic solvents. The reaction conveniently takes place in the temperature range from 0° to +80° C., preferably from +10° to +40° C. It is preferred to add an organic base. Examples of suitable bases are tertiary amines such as triethylamine, triethylenediamine, triazole and, preferably, pyridine, imidazole or 1,8-diazabicyclo-[5.4.0]-undec-7-ene (DBU).

The removal of these silyl and acyl radicals $R_1$ in the 5-position is effected by selective mild hydrolysis (→R=H) with e.g. arylsulfonic acid in alcoholic solution or in accordance with another method known to the skilled person.

The described process for the preparation of compounds of formula I constitutes in all its partial steps an object of the present invention.

The compounds of formula I are most suitable for controlling pests of animals and plants, including ectoparasites of animals. These last mentioned pests comprise those of the order Acarina, in particular pests of the families Ixodidae, Dermanyssidae, Sarcoptidae, Psoroptidae; of the orders Mallophaga, Siphonaptera, Anoplura (e.g. family of the Haematopinidae); and of the order Diptera, in particular pests of the families Muscidae, Calliphoridae, Oestridae, Tabanidae, Hippoboscidae, and Gastrophilidae.

The compounds of formula I can also be used against hygiene pests, especially of the order Diptera (families Sarcophagidae, Anophilidae and Culicidae); of the order Orthoptera, of the order Dictyoptera (e.g. family of the Blattidae), and of the order Hymenoptera (e.g. family of the Formicidae).

The compounds of formula I also have a lasting action against mites and insects which are parasites of plants. When used to control spider mites of the order Acarina, they are effective against eggs, nymphs and adults of Tetranychidae (Tetranychus spp. and Panonychus spp.) They also have excellent activity against sucking insects of the order Homoptera, in particular against pests of the families Aphididae, Delphacidae, Cicadellidae, Psyllidae, Coccidae, Diaspididae and Eriophyidae (e.g. the rust mite on citrus fruit); of the orders Hemiptera, Heteroptera and Thysanoptera; and against plant-feeding insects of the orders Lepidoptera, Coleoptera, Diptera and Orthoptera.

The compounds of formula I are also suitable for use against soil pests.

The compounds of formula I are therefore effective against all development stages of sucking and feeding insects in crops such as cereals, cotton, rice, maize, soybeans, potatoes, vegetables, fruit, tobacco, hops, citrus fruit, avocados and others.

The compounds of formula I are also effective against plant nematodes of the species Meloidogyne, Heterodera, Pratylenchus, Ditylenchus, Radolphus, Rhizoglyphus and others.

Furthermore, the compounds of formula I act against helminths, among which the endoparasitic nematodes can be the cause of severe diseases in mammals, e.g. non-humanoid warm-blooded animals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesphagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formula I is their activity against those parasites which are resistant to benzimidazole-based parasiticides.

Certain species of the genera Nematodirus, Cooperia and Oesophagostomum attack the intestinal tract of the host animal, whereas others of the species Haemonchus and Ostertagia parasiticise in the stomach and those of the species Dictyocaulus in the lung tissue. Parasites of the families Filariidae and Setariidae are found in internal cell tissue and internal organs, e.g. in the heart, blood vessels, lymph vessels and in subcutaneous tissue. In this connection, particular mention is to be made of the dog heartworm, *Dirofilaria immitis*. The compounds of formula I are highly effective against these parasites.

The compounds of formula I are also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compounds of this invention are also effective against parasites of the species Wuchereria, Brugia, Onchocerca and Loa of the family of the Filariidae which occur in the blood, in tissue and various organs, and, in addition, against Dracunculus and parasites of the species Strongyloides and Trichinella which infest in particular the gastro-intestinal tract.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 10 mg/kg of body weight, and are applied to enclosed crop areas, to pens, livestock buildings or other buildings in amounts of 10 g to 1000 g per hectare.

The formulations, i.e. the compositions, preparations or mixtures containing the compound of formula I (active ingredient) are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholiphids.

The surfactants customarily employed in the art of formulation are described e.g. in "McCutcheon's Detergents and Emulsifiers Annual", MC Publishing Corp. Ridgewood, N.J., 1982.

The pesticidal compositions usually contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1–10,000 ppm.

The present invention therefore also relates to pesticidal compositions which contain as active ingredient at least one compound of formula I, together with customary carriers and/or dispersing agents.

The compositions may also contain further ingredients such as stabilisers, antifoams, viscosity regulators, binders, tackifiers as well as fertilisers or other active ingredients for obtaining special effects.

PREPARATORY EXAMPLES

Preparation of starting materials and intermediates

Example S1

Preparation of 14,15-epoxymilbemycin D (formula VII)

While cooling with ice, a solution of 170 mg of chloroperbenzoic acid in 5 ml of dichloromethane is added to a solution of 550 mg of milbemycin D in 5 ml of dichloromethane. After stirring for 1 hour at 0° to 5° C., another 170 mg of the oxidising agent are added and stirring is continued for 30 minutes. When the reaction is complete, the solution is poured into an ice-cooled solution of sodium sulfite and extracted with ethyl acetate. The combined extracts are washed once with water, dried, and concentrated by evaporation in vacuo. The crude product is purified by chromatography through a column of silica gel (elution with a 20:15 mixture of n-hexane and ethyl acetate), affording 450 mg of amorphous, white 14,15-epoxymilbemycin D.

Example S2

Preparation of 15-hydroxy-$\Delta^{13,14}$-milbemycin D (formula IIb)

9.5 ml (0.41 g; 9.53 mmol) of a 6.96% solution of $HN_3$ in diethyl ether are added at −20° C. to a solution of 2.1 ml (1.75 g; 15.3 mmol) of triethyl aluminium in 8.5 ml of absolute diethyl ether. The reaction mixture is then added at −10° C. to 1.8 g (3.15 mmol) of 14,15-epoxymilbemycin D (in substance). The ensuing reaction is strongly exothermic. After 1 hour at room temperature, 4 ml of absolute ether are added and the gelatinous reaction mixture is vigorously stirred. After 4 hours, the reaction mixture is worked up as described in Example S1. Chromatography through 70 g of silica gel (elution with a 10:1 mixture of $CH_2Cl_2$ and acetone) affords 200 mg (10%) of 14-azido-15-hydroxymilbemycin D and 820 mg (45%) of 15-hydroxy-$\Delta^{13,14}$-milbemycin D; m.p. 151°–153° C. (recrystallisation from methanol).

Example S3

Preparation of 5-O-tert-butyldimethylsilyl-14,15-epoxymilbemycin D (formula VII)

A solution of 2.21 g (3.86 mmol) of 14,15-epoxymilbemycin D, 757 mg (5.02 mmol) of tert-butyldimethylchlorosilane and 342 mg (5.02 mmol) of imidazole in 4 ml of dimethylformamide is stirred for 90 minutes at room temperature. Then 80 ml of diethyl ether are added and the mixture is filtered through 20 g of silica gel and the filtrate is concentrated, affording 2.65 g (100%) of 5-O-tert-butyldimethyl- silyl-14,15-epoxymilbemycin D.

$^1$H-NMR (300 MHz., solvent CDCl$_3$., δ values based on Si(CH$_3$)$_4$=TMS). 0.12 ppm (s) (CH$_3$)$_2$Si—O—; 0.92 ppm (s) (t-C$_4$H$_9$)Si—O—; 1.23 ppm (broad s) (C$_{14}$CH$_3$, i.e. signal of the CH$_3$ group in the 14-position); 2.56 ppm (d; J=9) (C$_{15}$H, i.e. signal of the proton in the 15-position).

Following the same procedure, the corresponding 5-O-trimethylsilyl-14,15-epoxymilbemycin D (m.p. 92°-97° C.) can be prepared by reaction with trimethylsilyl trifluoromethanesulfonate.

Example S4

Preparation of 5-O-tert-butyldimethylsilyl-15-hydroxy-Δ$^{13,14}$-milbemycin D (formula IIb)

A solution of the HN$_3$/Et$_3$Al complex reagent (prepared from a solution of 4.97 ml of triethyl aluminium in 7 ml of absolute tetrahydrofuran and 9.15 ml of a 2.39 molar solution of HN$_3$ (21.9 mmol) in absolute diethyl ether) is added, under argon, to a solution of 5.0 g (7.29 mmol) of 5-O-tert-butyldimethylsilyl-14,15-epoxymilbemycin D in about 20 ml of absolute tetrahydrofuran, and the mixture is heated under reflux for 15 hours. Then 250 ml of ether, 2 ml of methanol, and finally a mixture of 10 g of Na$_2$SO$_4$.10H$_2$O and 10 g of celite are added at room temperature. The mixture is filtered and the filtrate is concentrated and chromatography of the crude product through 160 g silica gel (elution with 0–30% of ethyl acetate in hexane) affords 2.37 g (47%) of 5-O-tert-butyldiethylsilyl-15-hydroxy-Δ$^{13,14}$-milbemycin D.

$^1$H-NMR (300 MHZ, CDCl$_3$): 1.59 ppm (d; J=1) (C$_{14}$CH$_3$); 4.06 ppm (dd; J$_1$=11; J$_2$=4) (C$_{15}$H); 5.15 ppm (d; J=8) (C$_{13}$H).

In addition, 109 mg (2%) of 13β-azido-5-O-tert-butyldimethylsilylmilbemycin D are obtained.

Example S5

Preparation of 14,15-epoxymilbemycin A$_4$ (R$_2$=C$_2$H$_5$) (formula VII)

A solution of 2.43 g (14.08 mmol) of m-chloroperbenzoic acid in 70 ml of dichloromethane is added dropwise at room temperature to a solution of 5.7 g (10.5 mmol) of milbemycin A$_4$ in 140 ml of dichloromethane and 120 ml of a 0.5 molar solution of NaHCO$_3$. The mixture is vigorously stirred for 1 hour at room temperature and then diluted with 300 ml of dichloromethane. The organic phase is washed with an aqueous solution of NaHCO$_3$, dried over Na$_2$SO$_4$ and concentrated, affording 5.7 g of epoxide as crude product.

Example S6

Preparation of 5-O-tert-butyldimethylsilyl-14,15-epoxymilbemycin A$_4$ (formula VII)

5.7 g of 14,15-epoxymilbemycin A$_4$ are dissolved in 10 ml of dry dimethylformamide. Then 0.63 g (9.16 mmol) of imidazole and 1.4 g (9.34 mmol) of tert-butyldimethylchlorosilane are added at room temperature. The mixture is stirred for 1 hour at room temperature and chromatographed through 150 g of silica gel (elution with a 4:1 mixture of hexane and ether), affording 2.84 g (40% of theory, based on milbemycin A$_4$) of the silylated epoxy derivative.

Example S7

Preparation of 5-O-tert-butyldimethylsilyl-15-hydroxy-Δ$^{13,14}$-milbemycin A$_4$ (formula IIb)

The complex reagent HN$_3$/Al(ethyl)$_3$ is prepared as follows: To 2.8 ml (12.2 mmol) of Al(C$_2$H$_5$)$_3$ in 4 ml of absolute tetrahydrofuran are slowly added at about −20° C., under argon, 5.28 ml (20.4 mmol) of an 10% solution of HN$_3$ in absolute diethyl ether. To this solution is added, under argon, a solution of 2.84 g (4.25 mmol) of the compound obtained in Example S6, and the mixture so obtained is heated for 4 hours under reflux. Then 500 ml of diethyl ether and 10 g of Na$_2$SO$_4$.10H$_2$O and 10 g of celite are added at room temperature. The mixture is filtered and the filtrate is concentrated. Chromatography of the crude product through 100 g of silica gel (elution with a 7:2 mixture of hexane and diethyl ether) affords 1.72 g (60% of theory) of the title compound.

$^1$H-NMR (300 MHz, CDCl$_3$): 1.59 ppm (broad s) (C$_{14}$CH$_3$); 4.05 ppm (broad s) (C$_{15}$H); 5.15 ppm (d; J=6) C$_{13}$H).

In addition, 0.1 g of 13β-azido-5-O-tert-butyldimethylsilylmilbemycin A$_4$ is obtained.

Example S8

Preparation of 15-hydroxy-Δ$^{13,14}$-milbemycin A$_4$ (formula IIb)

Hydrolysis of 5 mg of the title compound of Example S7 with 1 ml of a 1% solution of p-toluenesulfonic acid in methanol and working up in diethyl ether with a 5% solution of sodium bicarbonate affords the title compound.

Example S9

Preparation of 14,15-epoxymilbemycin A$_3$ (R$_2$=CH$_3$) (formula VII)

In accordance with the procedure described in Example S1, reaction of 220 mg of milbemycin A$_3$ in 5 ml of dichloromethane and 320 mg of benzoperacid in 5 ml of dichloromethane at −2° to +5° C. over 1½ hours and purification through a column of silica gel affords 190 mg of 14,15-epoxymilbemycin A$_3$.

Example S10

Preparation of 5-O-tert-butyldimethylsilyl-14,15-epoxymilbemycin A$_3$ (formula VII)

In accordance with the procedure of Example S3, reaction of 190 mg of 14,15-epoxymilbemycin A$_3$ and 120 mg of tert-butyldimethylchlorosilane in the presence of imidazole affords 217 mg of the title compound.

Example S11

Preparation of 5-O-tert-butyldimethylsilyl-15-hydroxy-Δ$^{13,14}$-milbemycin A$_3$ (formula IIb)

In accordance with the epoxy cleavage of Example S4, 203 mg of the title compound are obtained from 210 mg of 5-O-tert-butyldimethylsilyl-14,15-epoxymilbemycin A$_3$, in absolute diethyl ether using the complex reagent $HN_3/Et_3Al$ under argon, and subsequent purification.

$^1$H-NMR (300 MHz, CDCl$_3$): 1.58 ppm (broad s) (C$_{14}$CH$_3$); 4.05 ppm (broad s) (C$_{15}$H); 5.15 ppm (d; J=6) (C$_{13}$H).

Example S12

Preparation of 15-hydroxy-$\Delta^{13,14}$-milbemycin A$_3$ (formula IIb)

In accordance with the procedure described in Example S1, the reagent $HN_3/Al(C_2H_5)_3$ is freshly prepared and added dropwise at $-10°$ C. to a solution of 830 mg (3.05 mmol) of 14,15-epoxymilbemycin A$_3$ in 7 ml of dry diethyl ether. After working up, 385 mg of 15-hydroxy-$\Delta^{13,14}$-milbemycin A$_3$ and 92 mg of 14-azido-15-hydroxymilbemycin A$_3$ are obtained.

Example S13

Preparation of 13-deoxy-14,15-epoxy-22,23-dihydroavermectin-B1a-aglycon (R$_2$=sec-C$_4$H$_9$) (formula VII)

In accordance with the procedure described in Example S5, 510 mg of the title compound are obtained from 520 mg of 13-deoxy-22,23-di- hydroavermectin-B1a-aglycon [Tetrahedron Letters, Vol. 24, No. 48, pp. 5333–5336 (1983)]and 210 mg of m-chlorobenzoperacid in 20 ml of dichloromethane.

Example S14

Preparation of 5-O-tert-butyldimethylsilyl-13-deoxy-14,15-epoxy-22,23-dihydroavermectin-B1a-aglycon (formula VII)

In accordance with the procedure described in Example S6, 108 mg of the title compound are obtained from 220 mg of the title compound of Example S13 and 55 mg of tert-butyldimethyldichlorosilane in the presence of 25 mg of imidazole in 5 ml of dry dimethylformamide.

Example S15

Preparation of 13-deoxy-15-hydroxy-$\Delta^{13,14}$-dihydroavermectin-B1a-aglycon (formula IIb)

In accordance with the procedure described in Example S2, 112 mg of the title compound are obtained by reacting 220 mg of the title compound of Example S14 with the complex reagent consisting of 320 mg of Al(C$_2$H$_5$)$_3$ and 110 mg of a 6.96% solution of HN$_3$ in a total of 16 ml of dry diethyl ether. In addition, 61 mg of 13-deoxy-14-azido-15-hydroxy-22,23-dihydroavermectin-B1a-aglycon are obtained.

Example S16

Preparation of 5-O-tert-butyldimethylsilyl-13$\beta$-hydroxymilbemycin D and 13$\beta$-hydroxymilbemycin D (formula IIa)

A solution comprising 286 mg (0.41 mmol) of 5-O-tert-butyldimethylsilyl-15-hydroxy-$\Delta^{13,14}$-milbemycin D and 209 mg (0.56 mmol) of pyridinium dichromate (PDC) in 3 ml of dimethylformamide (DMF) is stirred for 30 minutes at room temperature. 1 ml of isopropanol is subsequently added and the mixture is stirred for 5 minutes and then diluted with 50 ml of ether. After a further 10 minutes, the mixture is filtered through silica gel and the filtrate is concentrated. Chromatography of the crude product through 20 g of silica gel (elution with a 1:2 mixture of ether and hexane) affords 165 mg (57%) of 5-O-tert-butyldimethylsilyl-13$\beta$-hydroxymilbemycin D.

$^1$H-NMR (300 MHz; CDCl$_3$; TMS): 1.59 ppm (br.s) (C$_{14}$CH$_3$) 3.70 ppm (d; J=10) (C$_{13}$H).

105 mg (0.153 mmol) of the compound so obtained are stirred at room temperature in 1 ml of a 1% solution of p-toluenesulfonic acid in methanol for 1 hour. The mixture is diluted with 20 ml of ether, filtered through silica gel and the filtrate is concentrated. The residue is chromatographed through about 10 g of silica gel (elution with a 1:4 mixture of acetone and dichloromethane), affording 73 mg (83%) of 13$\beta$-hydroxymilbemycin D.

$^1$H-NMR (300 MHz; CDCl$_3$; TMS): 1.58 ppm (br.s) (C$_{14}$CH$_3$) 3.71 ppm (d; J=10) (C$_{13}$H).

Preparation of final products of formula I

Example P1

Preparation of 13$\beta$-methoxymilbemycin D

A solution of 106 mg (0.155 mmol) of 5-O-tert-butyldimethylsilyl-15-hydroxy-$\Delta^{13,14}$-milbemycin D in 5 ml of 1% methanolic toluenesulfonic acid is heated under reflux for 4 hours. The solvent is evaporated off, the residue is taken up in diethyl ether and the resultant solution is filtered through silica gel. Chromatography of the crude product (95 mg) through 20 g of silica gel (elution with a 2:3 mixture of ethyl acetate and hexane) affords 33 mg (36%) of 13$\beta$-methoxymilbemycin D with the following spectroscopic data:

$^1$H-NMR (300 MHz; CDCl$_3$; TMS): 1.48 ppm (s) (C$_{14}$CH$_3$) 1.87 ppm (s) (C$_4$CH$_3$) 3.10 ppm (d; J=9.8) (C$_{13}$H) 3.15 ppm (s) (OCH$_3$)

mass spectrum m/e: 586 (M$^+$, 0.7%, C$_{34}$H$_{50}$O$_7$), 568, 554, 514, 458, 426, 325, 307.

Example P2

Preparation of 5-O-tert-butyldimethylsilyl-13$\beta$-methoxymilbemycin D and 13$\beta$-methoxymilbemycin D 0.419 ml (406 mg; 3.83 mmol) of trimethyl orthoformiate are added dropwise at room temperature to a solution of 344 mg (0.501 mmol) of 5-O-tert-butyldimethylsilyl-15-hydroxy-$\Delta^{13,14}$-milbemycin D in 3 ml of a 1% solution of sulfuric acid in diethyl ether. After 10 minutes, the reaction mixture is worked up with 5% aqueous NaHCO$_3$ solution and diethyl ether. Chromatography of the crude product (327 mg) through 20 mg of silica gel (elution with a 1:100 mixture of acetone and dichloromethane [100 ml] and then with a 1:50 mixture of acetone and dichloromethane [250 ml]) affords 107 mg (31%) of 5-O-tert-butyldimethylsilyl-13$\beta$-methoxymilbemycin D which is stirred in 2 ml of a solution of 40% aqueous HF/acetonitrile (5:95) for 1 hour at room temperature. The reaction mixture is then worked up with 5% aqueous NaHCO$_3$ solution and diethyl ether. Chromatography of the crude product (75 mg) through 12 g of silica gel (elution with a 2:3 mixture of ethyl acetate and hexane) affords 71 mg of 13$\beta$-methoxymilbemycin D with the spectroscopic data indicated in Example P1.

The compounds of Examples P2a to P2c are also prepared by procedures analogous to that of Example P2.

Example P2a:

13β-Methoxymilbemycin A₄

$^1$H-NMR (250 MHz, CDCl₃, TMS) 3.16 (s) (CH₃O) 3.10 (d, J=10 Hz) (C₁₃ H)

mass spectrum (FD) m/e: 572 (M⁺, C₃₃H₄₈O₈) (D=Field Desorption)

Example P2b

13β-(9'-Hydroxy-1',4',7'-trioxanoylmilbemycin D $^1$H-NMR (300 MHz, CDCl₃, TMS) 1.49 (s) (C₁₄CH₃) 1.87 (s) (C₄CH₃) 5.18 (m) (C₁₅H)

Example P2c

13β-(1',4',7',10'-Tetraoxaundecyl)milbemycin D $^1$H-NMR (300 MHz, CDCl₃, TMS) 3.37 (s) (CH₃O) 5.17 (m) (C₁₅H)

mass spectrum m/e: 718 (M⁺, C₄₀H₆₂O₁₁), 700, 646, 590, 586, 567, 554, 536, 439.

Example P3

Preparation of 5-O-tert-butyldimethylsilyl-13β-ethoxymilbemycin D and 13β-ethoxysilbemycin D and 15-ethoxy-Δ$^{13,14}$-milbemycin D (a) 0.2 ml (225 mg; 1.39 mmol) of triethyl orthoacetate are added dropwise at room temperature to a solution of 264 mg (0.385 mmol) of 5-O-tert-butyldimethylsilyl-15-hydroxy-Δ$^{13,14}$-milbemycin D in 0.5 ml of a 1% solution of sulfuric acid in diisopropyl ether and 1 ml of diethyl ether. After 2 minutes, the reaction mixture is worked up with 5% aqueous NaHCO₃ and diethyl ether. Chromatography of the crude product (230 mg) through 20 g of silica gel (elution with a 16:84 mixture of diethyl ether and hexane) affords 164 mg (61%) of 5-O-tert-butyldimethylsilyl-13β-ethoxymilbemycin D and 34 mg (13%) of 5-O-tert-butyldimethylsilyl-15-ethoxy-Δ$^{13\ 14}$-milbemycin D.

$^1$H-NMR (300 MHz; CDCl₃; TMS) of 5-O-tert-butyldimethyl-15-ethoxy-Δ$^{13,14}$-milbemycin D: 1.50 ppm (s) (C₁₄CH₃) 1.78 ppm (s) (C₄CH₃) 3.56 ppm (dd, J=4.3 and 11.1), (C₁₅H) 5.08 ppm (dds, J=1.1 and 9.3), C₁₃H).

(b) 164 mg (0.230 mmol) of 5-O-tert-butyldimethylsilyl-13β-ethoxymilbemycin D prepared according to step a) are treated with a 1% solution of p-toluenesulfonic acid in methanol for 1 hour at room temperature. Working up with diethyl ether and 5% aqueous NaHCO₃ and chromatography through 20 g of silica gel (elution with a 2:3 mixture of ethyl acetate and hexane) affords 136 mg (99%) of 13β-ethoxymilbemycin D with the following spectroscopic data:

$^1$H-NMR (300 MHz, CDCl₃, TMS) 1.49 ppm (s) (C₁₄CH₃) 1.87 ppm (s) (C₄CH₃) 3.21 ppm (d, J=9.8), (C₁₃H) 3.29 ppm (AB-system, J=9.5; A=3.17, resolved into q; J=7.0; δ$_B$=3.40; resolved into q; J=7.0), (OCH₂CH₃).

Example P4

Preparation of 13β-phenylthiomilbemycin D

With stirring, 0.086 ml (77 mg; 0.472 mmol) of triethyl orthoacetate is added dropwise at room temperature to a solution of 162 mg (0.236 mmol) of 5-O-tert-butyldimethylsilyl-15-hydroxy-Δ$^{13,14}$-milbemycin D and 0.3 ml (323 mg; 2.93 mmol) of triphenol in 0.3 ml of dichloromethane and 0.1 ml of H₂SO₄/diisopropyl ether (1:9). After 2 minutes, the reaction mixture is worked up with 5% aqueous NaHCO₃ solution and diethyl ether. Chromatography of the crude product through 3 g of silica gel (elution with hexane [40 ml], with a 1:4 mixture of diethyl ether and hexane [25 ml] and then with a 2:3 mixture of diethyl ether and hexane [25 ml]) affords 110 mg of the crude product which is then stirred in 2 ml of a 1% solution of p-toluenesulfonic acid in methanol for 1 hour at room temperature. The reaction mixture is worked up with 5% aqueous NaHCO₃ solution and diethyl ether. Chromatography through 20 g of silica gel (elution with a 9:1 mixture of dichloromethane and acetone affords 33 mg (21%) of 13β-phenylthiomilbemycin D with the following spectroscopic data as well as 9 mg (5%) of 13β-ethoxymilbemycin D.

$^1$H-NMR (300 MHz; CDCl₃; TMS): 1.58 ppm (s) (C₁₄CH₃) 1.87 ppm (s) (C₄CH₃) 3.33 ppm (d; J=11.0) (C₁₃H) 4.78 ppm (ddd; J=1.1; 5.3 and 11.3) (C₁₅H) 7.2–7.4 ppm (m) (phenyl)

mass spectrum m/e: 664 (M⁺, C₃₉H₅₂O₇S) 646, 555, 554, 537, 385, 293, 275, 210, 209.

Example P5

Preparation of 13β-phenylthiomilbemycin D

With stirring and under argon, 0.060 ml (68 mg; 0.478 mmol) of boron trifluoride ethyl etherate is added dropwise at −10° C. to a solution of 139 mg (0.203 mmol) of 5-O-tert-butyldimethylsilyl-15-hydroxy-Δ$^{13,14}$-milbemycin D and 0.080 ml (86 mg; 0.782 mmol) of thiophenol in 5 ml of dichloroethane. After 10 minutes, the reaction mixture is worked up with diethyl ether and 5% aqueous NaHCO₃ solution. Chromatography of the crude product through 20 g of silica gel (elution with a 1:9 mixture of ethyl acetate and hexane [100 ml] and then with a 3:7 mixture of ethyl acetate and hexane [250 ml]) affords 37 mg (27%) of 13β-phenylthiomilbemycin D with the spectroscopic data indicated in Example P4.

The following compounds of Examples P5a to P5h can also be prepared by procedures analogous to that of Example P5:

Example P5a

13β-Ethylthiomilbemycin D $^1$H-NMR (250 MHz, CDCl₃, TMS) 2.27 (q, J=5Hz)(CH₂—S) 3.05 (d, J=10 Hz)(C₁₃H)

mass spectrum (FD) m/e: 616 (M⁺, C₃₅H₅₂O₇S)

Example P5b

13β-Isopropylthiomilbemycin D $^1$H-NMR (250 MHz, CDCl₃, TMS) 2.55 (m) [(CH₃)₂CH-S] 3.05 (d, J=10 Hz)(C₁₃H)

mass spectrum (FD) m/e: 630 (M⁺, C₃₆H₅₄O₇S)

Example P5c

13β-tert-Butylthiomilbemycin D $^1$H-NMR (300 MHz, CDCl₃, TMS) 1.29 (s) (S-tert-butyl) 1.59 (s) (C₁₄CH₃) 1.87 (s) (C₄CH₃) 3.12 (d, J=10 Hz)(C₁₃H)

mass spectrum m/e: 644 (M⁺, C₃₇H₅₆O₇S), 210, 209, 181, 151.

Example P5d

13β-tert-Butylthiomilbemycin A₄

$^1$H-NMR (250 MHz, CDCl₃, TMS) 1.62 (s) (S-tert-butyl) 3.15 (d, J=10 Hz)(C₁₃H)

mass spectrum (FD) m/e: 630 (M+, $C_{36}H_{54}O_7S$)

Example P5e

13β-(2'-Ethoxyethylthio)milbemycin D $^1$H-NMR (250 MHz, CDCl$_3$, TMS) 2.52 (m) (C$\underline{H_2}$—S) 3.07 (d, J=10 Hz)(C$_{13}$—H) 3.54 (m) ( C$\underline{H_2}$—O—C$\underline{H_2}$)

Example P5f

13β-Ethylthiomilbemycin A$_4$ $^1$H-NMR (250 MHz, CDCl$_3$, TMS) 2.36 (m) (C$\underline{H_2}$—S) 3.04 (d, J=10 Hz)(C$_{13}$—H)

mass spectrum (FD) m/e: 602 (M+, $C_{34}H_{50}O_7S$)

Example P5g

13β-(2'-Hydroxy)ethylthiomilbemycin D and, as by-product, 13β-(2'-mercaptoethoxy)milbemycin D*

$^1$H-NMR (250 MHz, CDCl$_3$, TMS) 2.57 (m) (C$\underline{H_2}$—S) 3.04 (d, J=10 Hz)(C$_{13}$H) 3.64 (m) (C$\underline{H_2}$—OH) *2.66 (m) (C$\underline{H_2}$—SH) *3.24 (d, J=10 Hz)(C$_{13}$H) *3.28 and 3.45 (2m)(C$\underline{H_2}$—OH)

Example P5h

13β-(2'-Mercaptoethoxy)ethylthiomilbemycin D $^1$H-NMR (250 MHz, CDCl$_3$, TMS) 2.53 (m) (C$_{13}$—S—C$\underline{H_2}$) 2.69 (m) (C$\underline{H}$—SH) 3.09 (d, J=10 Hz)(C$_{13}$H) 3.56 (m) (C$\underline{H_2}$OC$\underline{H_2}$)

mass spectrum m/e: 692 (M$^{30}$, $C_{37}H_{56}O_8S_2$), 674, 656, 564, 537, 415, 413.

Example P6

Preparation of 13β-p-chlorophenoxycarbonylthiomilbemycin D and 5-O-tert-butyldimethylsilyl-13β-p-chlorophenoxycarbonylthiomilbemycin D (a) With stirring and under argon, 0.036 ml (50 mg; 0.242 mmol) of p-chlorophenylchlorothionoformiate is added dropwise at −10° C. to a solution of 151 mg (0.220 mmol) of 5-O-tert-butyldimethylsilyl-15-hydroxy-Δ$^{13,14}$-milbemycin D and 0.089 ml (87 mg; 1.10 mmol) of pyridine in 3 ml of dichloromethane. After stirring for 100 minutes at room temperature, a further 0.036 ml of p-chlorophenylchlorothionoformiate is added dropwise. After a further hour, the reaction mixture is worked up with 5% aqueous NaHCO$_3$ solution and diethyl ether. Chromatography of the crude product through 20 g of silica gel affords 221 mg of crude 5-O-tert-butyldimethylsilyl-13β-p-chlorophenoxycarbonylthiomilbemycin D.

(b) 140 mg of this crude product prepared in accordance with step (a) are stirred in 1 ml of a solution of 40% aqueous HF/acetonitrile (5:95) for 1 hour at room temperature. Working up with 5% aqueous NaHCO$_3$ solution and diethyl ether and chromatography through 20 g of silica gel (elution with a 2:3 mixture of ethyl acetate and hexane) affords 69 mg (67%) of 13β-p-chlorophenoxycarbonylthiomilbemycin D with the following spectroscopic data:

$^1$H-NMR (300 MHz; CDCl$_3$; TMS) 1.87 ppm (s) (C$_4$CH$_3$) 3.83 ppm (d, J=11.7), (C$_{13}$H) 7.0–7.4 ppm (m) (phenyl)

mass spectrum m/e: 742 (M+, $C_{40}H_{51}O_9SCl$) 614, 555, 427, 277, 209, 181, 151.

Example P7

Preparation of 13β-mercaptomilbemycin D and 5-O-tert-butyldimethylsilyl-13β-mercaptomilbemycin D (a) With stirring and under argon, 0.1 ml (157 mg; 0.689 mmol) of trichloroethylchlorothionoformiate is added dropwise at −10° C. to a solution of 209 mg (0.305 mmol) of 5-O-tert-butyldimethylsilyl-Δ$^{13,14}$-milbemycin D and 0.012 ml (120 mg; 1.52 mmol) of pyridine in 3 ml of dichloromethane. After stirring for 1 hour at room temperature, the reaction mixture is worked up with 5% aqueous NaHCO$_3$ solution and diethyl ether. Chromatography of the crude product through 20 g of silica gel (elution with a 1:4 mixture of ethyl acetate and hexane) affords 282 mg of partially impure 5-O-tert-butyldimethylsilyl-13β-trichloroethoxycarbonylthiomilbemycin D.

A suspension of 320 mg (4.9 mmol) of zinc powder in a solution of 227 mg of this crude product in 0.5 ml of diethyl ether, 2 ml of 90% aqueous acetic acid and 3 drops of HCl (1 M) are stirred for 16 hours at room temperature under argon. The mixture is diluted with diethyl ether and filtered through celite and the filtrate is dried over MgSO$_4$ and concentrated. Chromatography of the crude product through 20 g of silica gel (elution with a 12:88 mixture of ethyl acetate and hexane) affords 72 mg (40%) of 5-O-tert-butyldimethylsilyl-13β-mercaptomilbemycin D.

(b) This purified product is stirred in 2 ml of a 1% solution of p-toluenesulfonic acid in methanol for 2 hours at room temperature. After working up with 5% aqueous NaHCO$_3$ solution and diethyl ether, the crude product is chromatographed through 20 g of silica gel (elution with a 2:3 mixture of ethyl acetate and hexane), affording 54 mg (89%) of 13β-mercaptomilbemycin D with the following spectroscopic data:

$^1$-NMR (300 MHz; CDCl$_3$; TMS) 1.61 ppm (s) (C$_{14}$CH$_3$) 1.87 ppm (s) (C$_4$CH$_3$) 3.31 ppm (dd; J=5.4 and 10.9), (C$_{13}$H)

mass spectrum m/e: 588 (M+, $C_{33}H_{48}O_7S$) 460, 309, 277, 209, 181.

Example P8

Preparation of 13β-methylthiomilbemycin D (a) With stirring and under argon, 422 mg (0.615 mmol) of 5-O-tert-butyldimethylsilyl-15-hydroxy-Δ$^{13,14}$-milbemycin D, 178 mg (1.23 mmol) of N-methylthiosuccinimide and 323 mg of (1.23 mmol) of triphenylphosphine are dissolved at room temperature in 3 ml of dimethyl disulfide. After 10 minutes, 0.4 ml of methanol is added and the solvent is evaporated off. The crude product is chromatographed through 20 g of silica gel (elution with a 1:9 mixture of ethyl acetate and hexane [200 ml] and then with a 2:3 mixture of ethyl acetate and hexane [250 ml]), affording 223 mg (53%) of 5-O-tert-butyldimethylsilyl-13β-methylthiomilbemycin D and, as by-products, 36 mg (9%) of 5-O-tert-butyldimethylsilyl-13Bhydroxymilbemycin D and 28 mg (7%) of 5-O-tert-butyldimethylsilyl-15-succinimido-Δ$^{13,14}$-milbemycin D.

(b) 160 mg (0.223 mmol) of the 5-O-tert-butyldimethylsilyl-13β-methylthiomilbemycin D so obtained are treated with 1% p-toluenesulfonic acid in methanol for 1 hour at room temperature. Working up with 5% aqueous NaHCOs solution and diethyl ether, and chromatography through 20 g of silica gel (elution with a 2:3 mixture of ethyl acetate and hexane) affords 119 mg (89% of 13β-methylthiomilbemycin D with the following spectroscopic data:

¹H-NMR (300 MHz; CDCl₃; TMS) 1.56 ppm (s) ($C_{14}CH_3$) 1.88 ppm (s) ($C_4CH_3$ and $SCH_3$) 2.90 ppm (d; J=11.0) ($C_{13}H$)

mass spectrum m/e: 602 (M⁺; $C_{34}H_{50}O_7S$), 474, 325, 323, 275, 210, 209.

The following compound of Example P8a can be prepared by a procedure analogous to that of Example P8:

Example P8a

13β-Methylthiomilbemycin A₄ ¹H-NMR (250 MHz; CDCl₃; TMS) 1.88 (s) ($CH_3S$) 2.92 (d, J=10 Hz)($C_{13}H$)

mass spectrum m/e 588 (M⁺, $C_{33}H_{48}O_7S$), 570, 530, 523, 461, 460, 413, 311, 309.

Example P9

Preparation of 13β-(2'-methoxyethoxymethoxy)-milbemycin D

With stirring, 75 μl (82 mg; 0.656 mmol) of 2-methoxyethoxymethyl chloride are added at room temperature to a solution of 150 mg (0.218 mmol) of 5-O-tert-butyldimethylsilyl-13β-hydroxymilbemycin D and 225 μl (170 mg; 1.312 mmol) of N,N-diisopropylethylamine in 0.5 ml of dichloromethane. After 3 days at room temperature, the reaction mixture is worked up with diethyl ether and 5% aqueous NaHCO₃ solution. The diethyl ether layer is dried over magnesium sulfate and filtered and the filtrate is concentrated. The oily crude product is stirred in 2 ml of a solution of 40% aqueous HF/acetonitrile (5:95) for 1 hour at room temperature and the reaction mixture is again worked up with 5% aqueous NaHCO₃ solution and diethyl ether. Yield: 125 mg of 13β-(2'-methoxyethoxymethoxy)-milbemycin D.

¹H-NMR (250 MHz, CDCl₃, TMS) 3.38 (s) ($CH_3O$) 3.55 (m) ($OCH_2CH_2O$) 4.62 (AB-sytem, $\delta_A$=4.56; $\delta_B$=4.68, J=7 Hz)($OCH_2O$)

mass spectrum (FD) m/e: 660 (M⁺, $C_{37}H_{56}O_{11}$).

Example p9a

13β-Methoxymethoxymilbemycin A₄

Preparation is by a procedure analogous to that of Example P9.

¹H-NMR (250 MHz, CDCl₃, TMS) 3.33 (s) ($CH_3O$) 3.63 (d, J=10 Hz)($C_{13}H$) 4.42 and 4.60 (2d, J=7 Hz)($OCH_2O$)

mass spectrum (FD) m/e: 602 (M⁺, $C_{34}H_{50}O_9$).

Example 9b

13β-Isobutylthio-milbemycin A₄

Preparation is by a procedure analogous to that of Example P9.

¹H-NMR (300 MHz; CDCl₃, TMS) 1.55 (m) [$(CH_3)_2C-S$]3.05 (d, J=10 Hz)($C_{13}H$)

mass spectrum (FD) m/e: 654 (M⁺, $C_{35}H_{52}O_7$)

The following compounds of formula I are also prepared by procedures analogous to those described in the foregoing Examples:

TABLE 1

Typical representatives of compounds of formula I, wherein $R_1$ is hydrogen ($C_6H_5$ is a phenyl group)

| Comp. No. | $R_2$ | R |
|---|---|---|
| 1.1 | $CH_3$ | $OCH_3$ |
| 1.2 | $C_2H_5$ | $OCH_3$ |
| 1.3 | $C_3H_7$—i | $OCH_3$ |
| 1.4 | $C_4H_9$—s | $OCH_3$ |
| 1.5 | $CH_3$ | $SCH_3$ |
| 1.6 | $C_2H_5$ | $SCH_3$ |
| 1.7 | $C_3H_7$—i | $SCH_3$ |
| 1.8 | $C_4H_9$—s | $SCH_3$ |
| 1.9 | $CH_3$ | $OC_2H_5$ |
| 1.10 | $C_2H_5$ | $OC_2H_5$ |
| 1.11 | $C_3H_7$—i | $OC_2H_5$ |
| 1.12 | $C_4H_9$—s | $OC_2H_5$ |
| 1.13 | $CH_3$ | $SC_2H_5$ |
| 1.14 | $C_2H_5$ | $SC_2H_5$ |
| 1.15 | $C_3H_7$—i | $SC_2H_5$ |
| 1.16 | $C_4H_9$—s | $SC_2H_5$ |
| 1.17 | $CH_3$ | $OC_6H_5$ |
| 1.18 | $C_2H_5$ | $OC_6H_5$ |
| 1.19 | $C_3H_7$—i | $OC_6H_5$ |
| 1.20 | $C_4H_9$—s | $OC_6H_5$ |
| 1.21 | $CH_3$ | $SC_6H_5$ |
| 1.22 | $C_2H_5$ | $SC_6H_5$ |
| 1.23 | $C_3H_7$—i | $SC_6H_5$ |
| 1.24 | $C_4H_9$—s | $SC_6H_5$ |
| 1.25 | $CH_3$ | Cl—(C₆H₄)—O—C(=O)—S— |
| 1.26 | $C_2H_5$ | Cl—(C₆H₄)—O—C(=O)—S— |
| 1.27 | $C_3H_7$—i | Cl—(C₆H₄)—O—C(=O)—S— |
| 1.28 | $C_4H_9$—S | Cl—(C₆H₄)—O—C(=O)—S— |
| 1.29 | $CH_3$ | SH |
| 1.30 | $C_2H_5$ | SH |
| 1.31 | $C_3H_7$—i | SH |
| 1.32 | $C_4H_9$—s | SH |
| 1.33 | $CH_3$ | $CCl_3CH_2$—O—C(=O)—S |
| 1.34 | $C_2H_5$ | $CCl_3CH_2$—O—C(=O)—S |
| 1.35 | $C_3H_7$—i | $CCl_3CH_2$—O—C(=O)—S |
| 1.36 | $C_4H_9$—s | $CCl_3CH_2$—O—C(=O)—S |
| 1.37 | $C_3H_7$—i | $SC_3H_7$—i |
| 1.38 | $C_3H_7$—i | $SC_4H_9$—t |
| 1.39 | $C_3H_7$—i | $OC_4H_9$—t |
| 1.40 | $C_3H_7$—i | $OC_3H_7$—i |
| 1.41 | $C_2H_5$ | $SC_4H_9$—t |
| 1.42 | $C_2H_5$ | $OC_4H_9$—t |
| 1.43 | $C_3H_7$—i | $SCH_2CH_2OC_2H_5$ |

TABLE 1-continued

Typical representatives of compounds of formula I, wherein $R_1$ is hydrogen ($C_6H_5$ is a phenyl group)

| Comp. No. | $R_2$ | R |
|---|---|---|
| 1.44 | $C_3H_7$—i | $SCH_2CH_2OH$ |
| 1.45 | $C_3H_7$—i | $SCH_2CH_2OCH_2CH_2SH$ |
| 1.46 | $C_3H_7$—i | $SC_4H_9$—n |
| 1.47 | $C_3H_7$—i | $O(CH_2CH_2O)_3CH_3$ |
| 1.48 | $C_3H_7$—i | $O(CH_2CH_2O)_3H$ |
| 1.49 | $C_3H_7$—i | $OCH_2OCH_2CH_2OCH_3$ |
| 1.50 | $C_3H_7$—i | $OCH_2CH_2SH$ |
| 1.51 | $C_2H_5$ | $OCH_2OCH_3$ |
| 1.52 | $C_2H_5$ | $O(CH_2CH_2O)_3CH_3$ |
| 1.53 | $C_2H_5$ | $SC(CH_3)_2CH_2CH_3$ |
| 1.54 | $C_2H_5$ | $O(CH_2CH_2O)_3H$ |
| 1.55 | $C_2H_5$ | $SC_4H_9$—n |
| 1.56 | $C_2H_5$ | $OC_4H_9$—n |
| 1.57 | $C_2H_5$ | $SCH_2C(CH_3)_3$ |
| 1.58 | $C_2H_5$ | $SCH_2CH_2C(CH_3)_3$ |
| 1.59 | $CH_3$ | $SCH_2C(CH_3)_3$ |
| 1.60 | $C_3H_7$—i | $SCH_2C(CH_3)_3$ |
| 1.61 | $CH_3$ | $SCH_2CH_2C(CH_3)_3$ |

This table implies no limitations.

Formulation Examples for active ingredients of formula I (throughout, percentage are by weight)

| Wettable powders | (a) | (b) | (c) |
|---|---|---|---|
| a compound 1.1 to 1.61 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| a compound 1.1 to 1.61 | 10% |
| octylphenol polyethylene glycol ether (4-5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| a compound 1.1 to 1.61 | 5% | 8% |
| talcum | 95% | — |
| kaolin | — | 92% |

Ready for use dusts are obtained by mixing the active ingredient with the carrier, and grinding the mixture in a suitable mill.

| Extruder granulate | |
|---|---|
| a compound 1.1 to 1.61 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Tablets or boluses | | |
|---|---|---|
| I | a compound 1.1 to 1.61 | 33.00% |
| | methyl cellulose | 0.80% |
| | highly dispersed silicic acid | 0.80% |
| | maize starch | 8.40% |

The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12M sieve and the granulate is dried.

| II | crystalline lactose | 22.50% |
|---|---|---|
| | maize starch | 17.00% |
| | microcrystalline cellulose | 16.50% |
| | magnesium stearate | 1.00% |

All 4 adjuvants are thoroughly mixed. Phases I and II are mixed and compressed to tablets or boluses.

If the compounds of formula I, or compositions containing them, are used for controlling endoparasitic nematodes, cestodes and trematodes in domestic animals and productive livestock, for example cattle, sheep, goats, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, boluses or capsules.

If the physical and toxicological properties of solutions or emulsions permit it, the compounds of formula I, or compositions containing them, can also be injected into animals for example subcutaneously, administered intraruminally or applied to the bodies of the animals by the pour-on method. Administration by means of salt licks or molasses blocks is also possible.

Biological Examples

B1: Insecticidal stomach poison action against *Spodoptera littoralis*

Potted cotton plants in the 5-leaf stage are sprayed with a solution containing 3, 12.5 or 50 ppm of the test compound in acetone/water. After the coating has dried, the plants are populated with about 30 larvae ($L_1$ stage) of *Spodoptera littoralis*. Two plants are used for each test compound and test species. The test is carried out at about 24° C. and 60% relative humidity. Evaluations and intermediate evaluations of moribund insects, larval growth and feeding damage are made after 24, 48 and 72 hours.

Complete kill was achieved after 24 hours with the compounds of formula I of the Preparatory Examples at a concentration of 6 ppm. Compounds 1.6, 1.38, 1.41, 1.47 and 1.48 achieved complete kill even at 3 ppm.

B2: Action against plant-destructive acarids: OP-sensitive *Tetranychus urticae*

16 hours before the start of the test, the primary leaves of bean plants (*Phaseolus vulgaris*) are infected with an infested piece of leaf from a mass culture of *Tetranychus urticae*. Upon removal of the piece of leaf, the plants infested with all stages of the mites are sprayed to drip point with a solution containing 0.4 ppm or 1.6 ppm of the test compound. The temperature in the greenhouse compartment is about 25° C.

The percentage of mobile stages (adults and nymphs) and of eggs is evaluated under a stereoscopic microscope after 7 days. Compounds of formula I, e.g. compound 1.38 or 1.47, achieved complete kill at a concentration of 0.4 ppm.

B3: Action against $L_1$ larvae of *Lucilia sericata*

1 ml of an aqueous suspension of test compound is mixed with 3 ml of a special larval culture medium at about 50° C. such that a homogeneous composition containing 250 ppm or 125 ppm is obtained. About 30 *Lucilia sericata* larvae ($L_1$) are put into each test tube containing active ingredient. A mortality count is made after 4 days. The compounds of the Preparatory Examples achieved complete kill at 250 ppm, and compounds 1.2, 1.6, 1.31, 1.37, 1.38, 1.41, 1.43, 1.49 and 1.51 achieved complete kill even at the reduced concentration of 100 ppm.

B4: Acaricidal action against *Boophilus microplus* (Biarra strain)

Adhesive tape is applied vertically across a PVC plate so that 10 fully replete female *Boophilus microplus* ticks (Biarra strain) can be affixed thereto with their backs, side by side, in a row. Each tick is injected from an injection needle with 1 μl of a liquid which contains a 1:1 mixture of polyethylene glycol and acetone, in which mixture a specific amount of test compound of 1, 0.1 or 0.01 μg per tick is dissolved. Control ticks are injected with liquid containing no test compound. After this treatment, the ticks are detached from the support and kept in an insectarium under normal conditions at about 28° C. and 80% relative humidity until oviposition has taken place and the larvae have hatched from the eggs of the control ticks. The activitiy of the test compound is determined with the $IR_{90}$, i.e. the effective dose is determined at which 9 out of 10 female ticks (90%) even after 30 days lay eggs from which larvae are unable to hatch.

Compounds 1.3, 1.6, 1.7, 1.11, 1.23, 1.31, 1.37, 1.38, 1.41 and 1.49 achieved an $IR_{90}$ of 0.5 μg.

B5: Trial with sheep infected with nematodes (*Haemonchus concortus* and *Trichostrongylus colubriformis*)

The test compound is administered in the form of a suspension with a stomach probe or by intraruminal injection to sheep which have been artificially infected with *Haemonchus concortus* and *Trichostrongylus colubriformis*. 1 to 3 animals are used for each dose. Each sheep is treated only once with a single dose of 1 mg or 0.2 mg/kg of body weight. Evaluation is made by comparing the number of worm eggs excreted in the faeces of the sheep before and after treatment.

Untreated sheep infected simultaneously and in the same manner are used as controls. In comparison with untreated and infected control groups, there is no nematode infestation (=complete reduction of the number of worm eggs in the faeces) in sheep which have been treated with one of tha compounds of formula I at 1 mg/kg. Compounds 1.3, 1.6, 1.7, 1.11, 1.15, 1.27, 1.31 and 1.37 achieved this activity even at 0.2 mg/kg.

B6: Contact action against *Aphis craccivora*

Pea plantlets which have been infested with all development stages of the aphid are sprayed with a solution prepared from an emulsifiable concentrate of the test compound and containing 50 ppm, 25 ppm or 12.5 ppm of active ingredient. After 3 days evaluation is made to establish whether at least 80% of the aphids are dead or have dropped from the plants. A composition is only rated as effective at this level of activity.

Compounds 1.2, 1.6, 1.7, 1.37, 1.41 and others achieved complete kill (=100%) at a concentration of 12.5 ppm.

B7: Larvicidal action against *Aëdes aegypti*

A 0.1% solution of the test compound in acetone is pipetted onto the surface of 150 ml of water in beakers in amounts sufficient to give concentrations of 10 ppm, 3.3 ppm and 1.6 ppm. After the acetone has evaporated, 30 to 40 three-day-old larvae of *Aedes aegypti* are put into each beaker. Mortality counts are made after 1, 2 and 5 days.

In this test, the compounds of the Preparatory Examples, e.g. compounds 1.3, 1.11, 1.27, 1.37, 1.38, 1.41, 1.47 and 1.48, achieved complete kill of all larvae at a concentration of 1.6 ppm after 1 day.

What is claimed is:

1. A compound of formula I

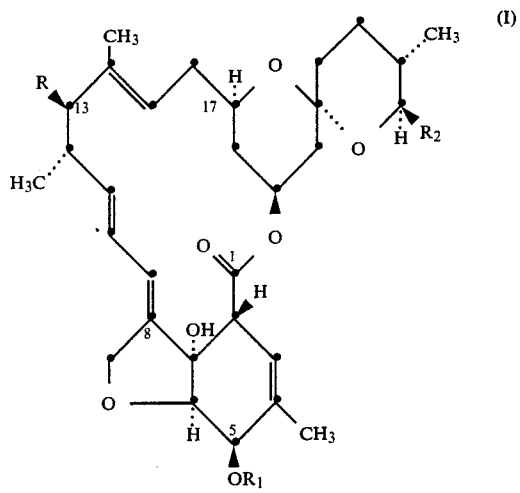

wherein
$R_1$ is hydrogen or an acyl or silyl protecting group;
$R_2$ is methyl, ethyl, isopropyl or sec-butyl; and
R is a radical $R_3$ which is bound through sulfur and is selected from the group consisting of $C_1$–$C_{10}$-alkyl, $C_1$-$C_{10}$haloalkyl, $C_1$-$C_{10}$hydroxyalkyl, $C_1$-$C_{10}$mercaptoalkyl, $C_2$-$C_{10}$alkoxyalkyl, $C_3$-$C_{10}$alkoxyalkoxyalkyl, hydroxy- or mercapto-substituted $C_3$-$C_{10}$alkoxyalkoxyalkyl, $C_4$-$C_{10}$alkoxyalkoxyalkyl, hydroxy- or mercapto-substituted $C_4$-$C_{15}$alkoxyalkoxyalkyl, $C_2$-$C_{10}$-alkenyl, $C_2$-$C_{10}$haloalkenyl, $C_2$-$C_{10}$alkynyl, $C_2$-$C_{10}$haloalkynyl, phenyl which is unsubstituted or substituted by halogen, $C_1$-$C_3$-alkyl, $C_1$-$C_3$haloalkyl, $C_1$-$C_3$alkoxy, $C_1$-$C_3$haloalkoxy, cyano and/or nitro, and benzyl which is unsubstituted or substituted by halogen, $C_1$-$C_3$alkyl, $C_1$-$C_3$haloalkyl, $C_1$-$C_3$alkoxy, $C_1$-$C_3$haloalkoxy, cyano and/or nitro, or R is one of the groups —SH or —S—C(O)OR$_4$, wherein R$_4$ is $C_1$-$C_{10}$alkyl, $C_1$-$C_{10}$haloalkyl, or a phenyl or benzyl group which is unsubstituted or substituted by halogen, $C_1$-$C_3$alkyl, $C_1$-$C_3$haloalkyl, $C_1$-$C_3$alkoxy, $C_1$-$C_3$haloalkoxy, cyano and/or nitro.

2. A compound of formula I according to claim 1, wherein R$_1$ is hydrogen or an acyl or silyl protecting group; R$_2$ is methyl, ethyl, isopropyl or sec-butyl; and R is a radical R$_3$ which is bound through sulfur and is selected from the group consisting of $C_1$-$C_{10}$alkyl, $C_1$-$C_{10}$haloalkyl, $C_2$-$C_{10}$alkoxyalkyl, $C_3$-$C_{10}$alkoxyalkoxyalkyl, $C_1$-$C_{10}$alkenyl, $C_1$-$C_{10}$haloalkenyl, $C_2$-$C_{10}$alkynyl, $C_2$-$C_{10}$haloalkynyl, phenyl which is unsubstituted or substituted by halogen, $C_1$-$C_3$alkyl, $C_1$-$C_3$haloalkyl, $C_1$-$C_3$alkoxy, $C_1$-$C_3$haloalkoxy, cyano and/or nitro, and benzyl which is unsubstituted or substituted by halogen, $C_1$-$C_3$alkyl, $C_1$-$C_3$haloalkyl, $C_1$-$C_3$alkoxy, $C_1$-$C_3$haloalkoxy, cyano and/or nitro, or R is one of the groups —SH or —S—C(O)OR$_4$, wherein R$_4$ is $C_1$-$C_{10}$alkyl, $C_1$-$C_{10}$haloalkyl, or a phenyl or benzyl group which is unsubstituted or substituted by halogen, $C_1$-$C_3$alkyl, $C_1$-$C_3$haloalkyl, $C_1$-$C_3$alkoxy, $C_1$-$C_3$haloalkoxy, cyano and/or nitro.

3. A compound of formula I according to claim 2, wherein R$_1$ is hydrogen or one of the groups R$_4$—C(O) or —Si(R$_5$)(R$_6$)(R$_7$), wherein each of R$_5$, R$_6$ and R$_3$ independently is $C_1$-$C_4$alkyl, benzyl or phenyl and the substituents R$_2$, R, R$_3$ and R$_4$ are as defined for formula I.

4. A compound of formula I according to claim 3, wherein R$_1$ is hydrogen; R$_2$ is methyl, ethyl, isopropyl or sec-butyl; and R is a radical R$_3$ which is bound through sulfur and is selected from the group consisting of $C_1$-$C_4$alkyl, $C_2$-$C_4$alkenyl, phenyl which is unsubstituted or substituted by fluorine, chlorine, bromine, methyl, CF$_3$, methoxy, cyano and/or nitro, and benzyl which is unsubstituted or substituted by fluorine, chlorine, bromine, methyl, CF$_3$, methoxy, cyano and/or nitro, or R is one of the groups —SH or —S—C(O)OR$_4$, wherein R$_4$ is $C_1$-$C_4$alkyl, $C_1$-$C_4$haloalkyl, or a phenyl or benzyl group each of which is unsubstituted or substituted by fluorine, chlorine, bromine, methyl, CF$_3$, methoxy, cyano and/or nitro.

5. A compound of formula I according to claim 4, wherein R$_1$ is hydrogen; R$_2$ is methyl, ethyl, isopropyl or sec-butyl; and R is a radical R$_3$ which is bound through sulfur and is selected from the group consisting of $C_1$-$C_4$alkyl and $C_2$-$C_4$alkenyl, or R is one of the groups —SH or —S—C(O)OR$_4$, wherein R$_4$ is $C_1$-$C_4$alkyl, $C_1$-$C_4$haloalkyl, or phenyl which is unsubstituted or substituted by fluorine, chlorine, bromine, methyl, CF$_3$, methoxy, cyano and/or nitro.

6. A compound of formula I according to claim 5, wherein R$_1$ is hydrogen; R$_2$ is methyl, ethyl, isopropyl or sec-butyl; and R is a radical R$_3$ which is bound through sulfur and is selected from the group consisting of $C_1$-$C_4$alkyl and $C_2$-$C_4$alkenyl, or R is one of the groups —SH or —S—C(O)OR$_4$, wherein R$_4$ is $C_1$-$C_4$alkyl or $C_1$-$C_4$haloalkyl.

7. A compound of formula I according to claim 6, wherein R$_1$ is hydrogen; R$_2$ is ethyl or isopropyl; and R is a radical R$_3$ which is bound through sulfur and is $C_1$-$C_2$alkyl, or R is one of the groups —SH or —S—C(O)OR$_4$, wherein R$_4$ is $C_1$-$C_2$alkyl or $C_1$-$C_2$haloalkyl.

8. A compound of formula I according to claim 7, wherein R$_1$ is hydrogen; R$_2$ is ethyl or isopropyl; and R is a radical R$_3$ which is bound through sulfur and is methyl, or R is one of the groups —SH or —S—C(O)OR$_4$, wherein R$_4$ is methyl.

9. A compound of formula I according to claim 6, wherein R$_1$ is hydrogen; R$_2$ is ethyl or isopropyl; and R is a radical R$_3$ which is bound through sulfur and is straight chain or branched $C_1$-$C_4$alkyl.

10. A compound of formula I according to claim 2, selected from the group consisting of
13β-phenylthiomilbemycin D,
13β-p-chlorophenoxycarbonylthiomilbemycin D,
13β-mercaptomilbemycin D,
13β-methylthiomilbemycin D,
13β-tert-butylthiomilbemycin D,
13β-methylthiomilbemycin A$_4$,
13β-tert-butylthiomilbemycin A$_4$,
13β-ethylthiomilbemycin A$_4$.

11. A compound of formula I according to claim 2, selected from the group consisting of
5-O-tert-butyldimethylsilyl-13β-mercaptomilbemycin D and
5-O-tert-butyldimethylsilyl-13β-methylthiomilbemycin D.

12. A pesticidal composition for controlling ectoparasites, endoparasites and insects, which composition contains an effective amount of at least one compound of formula I

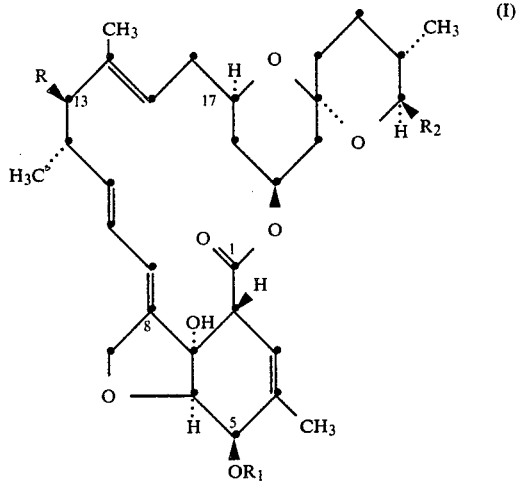

wherein
R$_1$ is hydrogen or an acyl or silyl protecting group;
R$_2$ is methyl, ethyl, isopropyl or sec-butyl; and
R is a radical R$_3$ which is bound through sulfur and is selected from the group consisting of $C_1$-$C_{10}$alkyl, $C_1$-$C_{10}$haloalkyl, $C_1$-$C_{10}$hydroxyalkyl, $C_1$-$C_{10}$mercaptoalkyl, $C_2$-$C_{10}$alkoxyalkyl, $C_3$-$C_{10}$alkoxyalkoxyalkyl, hydroxy- or mercapto-substituted $C_3$-$C_{10}$alkoxyalkoxyalkyl, $C_4$-$C_{15}$alkoxyalkoxyalkoxyalkyl, hydroxy- or mercapto-substituted $C_1$-$C_{10}$alkoxyalkoxyalkyl, $C_1$-$C_{10}$-alkenyl, $C_2$-$C_{10}$haloalkenyl, $C_2$-$C_{10}$alkynyl, $C_2$-$C_{10}$haloalkynyl, phenyl which is unsubstituted or substituted by halogen, $C_1$-$C_3$-alkyl, $C_1$-$C_3$haloalkyl, $C_1$-$C_3$alkoxy, $C_1$-$C_3$haloalkoxy, cyano and/or nitro, and benzyl which is unsubstituted or substituted by halogen, $C_1$-$C_3$-alkyl, $C_1$-$C_3$haloalkyl, $C_1$-$C_3$alkoxy, $C_1$-$C_3$haloalkoxy, cyano and/or nitro, or R is one of the groups —SH or —S—C(O)OR$_4$, wherein R$_4$ is $C_1$-$C_{10}$alkyl, $C_1$-$C_{10}$haloalkyl, or a phenyl or benzyl group which is unsubstituted or substituted by halogen, $C_1$-$C_3$alkyl, $C_1$-$C_3$haloalkyl, $C_1$-$C_3$alkoxy, $C_1$-$C_3$haloalkoxy, cyano and/or nitro,
together with customary carriers and/or dispersing agents.

13. A method of controlling pests of animals and plants, which method comprises applying or administering to the animal or applying to the plant or to the locus of said pests an effective amount of a compound of formula I according to claim 1.

14. A method according to claim 13, wherein the pests to be controlled are ectoparasites, endoparasites or insects.

15. A method according to claim 13, which method comprises controlling endoparasites in non-humanoid warm-blooded animals.

* * * * *